United States Patent
Vadake Kulangara et al.

(10) Patent No.: US 10,400,048 B2
(45) Date of Patent: Sep. 3, 2019

(54) CATALYST COMPRISING A METALLOCENE COMPLEX AND A CO-CATALYST

(71) Applicant: SABIC GLOBAL TECHNOLOGIES B.V., Bergen op Zoom (NL)

(72) Inventors: Shaneesh Vadake Kulangara, Roermond (NL); Nicolaas Hendrika Friederichs, Brunssum (NL); Anton Ginzburg, Heerlen (NL); Luca Rongo, Roermond (NL); Alexander Z. Voskoboynikov, Moscow (RU); Vyatcheslav V. Izmer, Moscow (RU); Dmitry S. Kononovich, Moscow (RU); Oleg Samsonov, Moscow (RU); Abbas-Alli Ghudubhai Shaikh, Bengaluru (IN); Vincenzo Busico, Naples (IT); Roberta Cipullo, Naples (IT); Ilya Borisov, Moscow (RU); Anamitra Chatterjee, Bengaluru (IN); Dmitry Uborsky, Moscow (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 61 days.

(21) Appl. No.: 15/579,621

(22) PCT Filed: May 24, 2016

(86) PCT No.: PCT/EP2016/061693
§ 371 (c)(1),
(2) Date: Dec. 5, 2017

(87) PCT Pub. No.: WO2016/188999
PCT Pub. Date: Dec. 1, 2016

(65) Prior Publication Data
US 2018/0148522 A1    May 31, 2018

Related U.S. Application Data

(60) Provisional application No. 62/180,283, filed on Jun. 16, 2015.

(30) Foreign Application Priority Data

May 27, 2015  (EP) ..................................... 15169418

(51) Int. Cl.
| C07F 17/00 | (2006.01) |
| C08F 4/6592 | (2006.01) |
| C08F 210/16 | (2006.01) |
| C08F 10/02 | (2006.01) |
| C08F 10/00 | (2006.01) |
| C08F 4/659 | (2006.01) |

(52) U.S. Cl.
CPC .............. *C08F 10/02* (2013.01); *C07F 17/00* (2013.01); *C08F 4/6592* (2013.01); *C08F 10/00* (2013.01);
(Continued)

(58) Field of Classification Search
CPC ................. C07F 17/00; C08F 210/16
See application file for complete search history.

(56) References Cited

U.S. PATENT DOCUMENTS

| 5,132,262 A | 7/1992 | Rieger et al. |
| 6,096,912 A | 8/2000 | Karl et al. |
(Continued)

FOREIGN PATENT DOCUMENTS

| EP | 1059300 A1 | 12/2000 |
| WO | 2014139949 A1 | 9/2014 |

OTHER PUBLICATIONS

Doerpinghaus et al., "Separating the effects of sparse long-chain branching on rheology from those due to molecular weight in polyethylenes" J. Rheol. 47(3), 2003, 20 pages.
(Continued)

*Primary Examiner* — Caixia Lu
(74) *Attorney, Agent, or Firm* — Cantor Colburn LLP

(57) ABSTRACT

The invention relates to a metallocene complex according to formula I

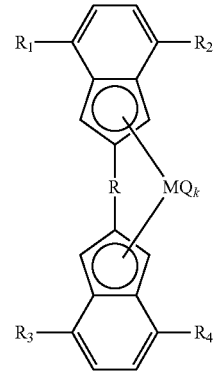

Formula I wherein
M is a metal selected from lanthanides or transition metals from group 3, 4, 5 or 6 of the Periodic System of the Elements,
Q is an anionic ligand to M,
k is the number of Q groups and equals the valence of M minus 2,
R is a bridging group containing at least one carbon atom bonded to the indenyl moiety at 2-position,
$R_1$, $R_2$, $R_3$ and $R_4$ are each independently chosen from the group consisting of H, a halogen atom and a C1-C20 hydrocarbylgroup, and wherein at least one of $R_1$ and $R_2$ is not H, and at least one of $R_3$ and $R_4$ is not H.

The invention also relates to a catalyst comprising the metallocene complex, to a process for making polyolefins and to the use of the polyolefins for making articles.

18 Claims, No Drawings

(52) U.S. Cl.
CPC ...... *C08F 4/65912* (2013.01); *C08F 4/65916* (2013.01); *C08F 210/16* (2013.01); *C08F 2410/02* (2013.01)

(56) References Cited

U.S. PATENT DOCUMENTS 6,342,622 B1  1/2002  Arts et al.
6,541,548 B2  4/2003  Weidner et al.

OTHER PUBLICATIONS

International Search Report for International Application No. PCT/EP2016/061693, International Filing Date May 24, 2016, dated Jul. 13, 2016, 5 pages.
Peacock, A., "Handbook of Polyethylene"; Marcel Dekker, Inc. ISBN: 0-8247-9546-6, 2000, pp. 43-66.
Randall et al. "A Review of High Resolution Liquid Carbon Nuclear Magnetic Resonance Characterizations of Ethylene-Based Polymers", Journal of Macromolecular Science—Reviews in Macromolecular Chem & Phys, C29 vol. 2 & 3, 1989, 16 pages.
Rudin, A., "Measurement of Long-Chain Branch Frequency in Synthetic Polymers" Modern Methods of Polymer Characterization, Chapter 3, 1991, 12 pages.
Schaverien et al., "Ethylene Bis(2-indenyl) Zirconocenes: A New Class of Diastereomeric Metallocenes for the (Co) Polymerization of alpha-Olefins", Organometallics, vol. 20, No. 16, 2001, 17 pages
Written Opinion for International Application No. PCT/EP2016/061693, International Filing Date May 24, 2016, dated Jul. 13, 2016, 6 pages.
Zimm et al., "The Dimensions of Chain Molecules Containing Branches and Rings", Journal of Chemical Phyics, vol. 17, No. 12, 1949, 15 pages.

CATALYST COMPRISING A METALLOCENE COMPLEX AND A CO-CATALYST

This application is a national stage application of PCT/EP2016/061693 filed May 24, 2016, which claims priority to European Patent Application 15169418.9 filed May 27, 2015, and U.S. Provisional Patent Application 62/180,283 filed Jun. 16, 2015, all of which are hereby incorporated by reference in their entirety.

The invention relates to a metallocene complex, to a catalyst comprising the metallocene complex, a co-catalyst and optionally an inorganic support material, a process for the preparation of the catalyst, a process for the preparation of olefin polymers by polymerizing one or more olefins in the presence of the catalyst and the use of the olefin polymers.

The catalyst that is used in a process for the preparation of olefin polymers comprises a bridged metallocene complex. Bridged metallocene complexes are known according to the state of the art and are for instance described in U.S. Pat. Nos. 6,342,622, 6,541,548, 5,132,262 and 6,096,912.

U.S. Pat. No. 6,342,622 describes bridged indenyl metallocene complexes comprising at least one indenyl group and a bridge comprising at least one sp2-hybridized carbon atom that is bonded to the indenyl group at the 2-position.

U.S. Pat. No. 6,541,548 describes bridged bis(tetrahydroindenyl) metallocene complexes wherein a divalent group bridges the two tetrahydroindenyl groups.

U.S. Pat. No. 5,132,262 describes bridged metallocene complexes wherein the bridge comprises silicon or germanium. The metallocene complexes are used for the preparation of propylene homo- and copolymers.

U.S. Pat. No. 6,096,912 describes bridged metallocene complexes wherein the bridge comprises carbon, sulfur, phosphorus, silicon or germanium. The metallocene complexes are used for the preparation of propylene homo- and copolymers.

WO2014139949 describes bridged 2-indenyl metallocene complexes wherein the bridge comprises a sp2 hybridized carbon atom.

A disadvantage of known catalysts comprising bridged metallocene complexes is that these catalysts produce low molecular weight copolymers when the catalysts are used for a copolymerization of ethylene with an α-olefin. There is a need for catalysts that can produce high molecular weight copolymers of ethylene and α-olefins. Also there is a need for catalysts that have a high affinity for α-olefins, like for example propylene, butene, hexene and octene, to make low density polyethylenes, or to incorporate α-olefins with high efficiency into polyolefins.

The invention relates to a metallocene complex according to formula I

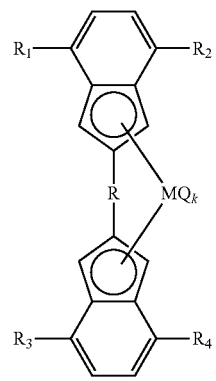

formula I wherein M is a metal selected from lanthanides or transition metals from group 3, 4, 5 or 6 of the Periodic System of the Elements,
Q is an anionic ligand to M,
k is the number of Q groups and equals the valence of M minus 2,
R is a bridging group containing at least one carbon atom bonded to the indenyl moiety at 2-position,
$R_1$, $R_2$, $R_3$ and $R_4$ are each independently chosen from the group consisting of hydrogen (H), a halogen atom and a C1-C20 hydrocarbylgroup, wherein at least one of $R_1$ and $R_2$ is not H, and at least one of $R_3$ and $R_4$ is not H.

The invention further relates to a catalyst comprising
a. the metallocene complex described above
b. a co-catalyst and
c. optionally an inorganic support material.

It has been surprisingly discovered that by using a catalyst according to the invention for the preparation of olefin polymers, olefin polymers are obtained with a high weight average molecular weight (Mw) and a high number average molecular weight (Mn), and especially the incorporation of an α-olefin is far more efficient compared to metallocene based catalyst systems known from the prior art. A further advantage is that the catalyst according to the invention can prepare copolymers of ethylene with α-olefins having 3 or more carbon atoms wherein the copolymers have a high α-olefin content.

The catalyst according to the invention comprises a metallocene complex, a co-catalyst and optionally an inorganic support material.

The metallocene complex used to prepare the catalyst is a metallocene complex according to formula I

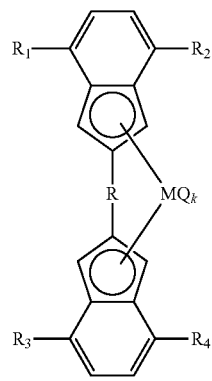

Formula I wherein
M is a metal selected from lanthanides or transition metals from group 3, 4, 5 or 6 of the Periodic System of the Elements,
Q is an anionic ligand to M,
k is the number of Q groups and equals the valence of M minus 2,
R is a bridging group containing at least one carbon atom bonded to the indenyl moiety at 2-position,
$R_1$, $R_2$, $R_3$ and $R_4$ are each independently chosen from the group consisting of hydrogen (H), a halogen atom and a C1-C20 hydrocarbylgroup, wherein at least one of $R_1$ and $R_2$ is not hydrogen, and at least one of $R_3$ and $R_4$ is not hydrogen.

The metallocene complex comprises a metal selected from lanthanides or transition metals from group 3, 4, 5 or 6 of the Periodic System of the Elements. The Periodic System of the Elements is understood to be the Periodic System of the Elements that can be found at www.chemicool.com. The metal M is preferably chosen from the group consisting of Ti, Zr, Hf, V and Sm, more preferably from Ti, Zr and Hf, most preferably the metal is Zr.

Q is an anionic ligand to M. The Q ligands preferably are the same and are selected from the group consisting of halogen (F, Cl, Br, I) and alkyl groups comprising 1 to 20 carbon atoms. More preferably the Q ligands are Cl or a methyl group.

k is the number of Q groups and equals the valence of M minus 2; k is an integer. Preferably, k is 2.

R is a bridging group comprising at least one carbon atom. R is bridging between the two carbon atoms at the 2-position of each of the two indenyl ligands in the metallocene complex. R can contain both sp3 and sp2 hybridized carbon atoms. However, preferably at least one sp2 hybridized carbon atom is present in the bridging group. The sp2 hybridized carbon atom is bonded to the carbon atom at the 2-position of one of the two indenyl ligands in the metallocene complex.

Examples of bridging groups are vinylene, vinylidene, propenylene, hexenylene, phenylene, cyclopropenylene, cyclobutenylene, cyclopentenylene, cyclohexenylene, cyclohexadienylene, tolylene, benzylene, naphthylene, anthrylene, pyrenylene, biphenylene and binaphthylene. The bridging group can be substituted with alkyl groups having 1 to 10 carbon atoms, for example the substituents may be selected from the group of methyl, ethyl, n-propyl, n-butyl, n-pentyl or n-hexyl. Preferably, R carries less than 10 substituents, more preferably less than 5 substituents and most preferably no substituents. R preferably is chosen from the group consisting of a biphenylene group or a substituted biphenylene group. Most preferably R is chosen from the group consisting of a 1,2 phenylene-group, a 2,2'-biphenylene group or a substituted 2.2'-biphenylene group.

$R_1$, $R_2$, $R_3$ and $R_4$ are identical or different and can be chosen from the group consisting of hydrogen; halogen; alkyl groups comprising 1-20 carbon atoms; or cycloalkyl, alkylaryl, aryl or arylalkyl groups comprising 5-20 carbon atoms, wherein at least one of $R_1$ and $R_2$ is not H, and at least one of $R_3$ and $R_4$ is not H.

Examples of halogen groups are F, Cl, Br and I.

Examples of alkyl groups are methyl, ethyl, propyl, butyl, hexyl and decyl. Examples of cycloalkyl groups are cyclopropane, cyclopentane and cyclohexane. Examples of alkylaryl groups are benzyl, pentamethylbenzyl and trityl. Examples of aryl groups are phenyl, indenyl, naphtyl and fluorenyl. Examples of arylalkyl substituents are xylyl, mesityl, tolyl and cumyl. Preferably, the substituents $R_1$, $R_2$, $R_3$ and $R_4$ are independently chosen from the group consisting of H, F, Cl, hydrocarbyl groups comprising 1-20 carbon atoms. Most preferably the substituents $R_1$, $R_2$, $R_3$ and $R_4$ are chosen from the group consisting of H, F, Cl, methyl, ethyl and phenyl.

The catalyst according to the invention comprises the metallocene complex described above and a co-catalyst. The co-catalyst employed according to the present invention can be an aluminium- or boron-containing co-catalysts. Suitable aluminium-containing co-catalysts comprise aluminoxanes and alkyl aluminium. The aluminoxanes usable according to the present invention are well known and preferably comprise oligomeric linear and/or cyclic alkyl aluminoxanes represented by the formula: $R^6-(AlR^6-O)_n-AlR^6_2$ for oligomeric, linear aluminoxanes and $(-AlR^6-O-)_m$ for oligomeric, cyclic aluminoxanes; wherein n is 1-40, preferably n is 10-20; m is 3-40, preferably m is 3-20 and $R^6$ is a $C_1$ to $C_8$ alkyl group and preferably a methyl group. Further other organoaluminum compounds can be used such as trimethylaluminum, triethylaluminium, triisopropylaluminum, tri-n-propylaluminum, triisobutylaluminum, tri-n-butylaluminum, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride, di-n-butylaluminium hydride and tetra-isobutyl-aluminoxane.

Suitable boron-containing co-catalysts include trialkylboranes, for example trimethylborane or triethylborane and/or perfluorophenylborane and/or a perfluorophenylborate.

In the process for the preparation of olefin polymers by polymerizing one or more olefins in the presence of a catalyst, preferably an organoaluminum co-catalyst is present.

More preferably, methylaluminoxane (MAO) is used as the co-catalyst.

In one embodiment a catalyst is formed from the metallocene complex as described above and the co-catalyst. This catalyst may be used, for example, in a solution polymerization of olefins.

In a preferred embodiment, the catalyst comprises an inorganic support material.

When a support material is present, the support material is preferably an inert support material, more preferably a porous inert support material. Examples of porous inert support materials are talc and inorganic oxides. Preferably, the support material is in a finely divided form.

Suitable inorganic oxide materials include group 2A, 3A, 4A and 4B metal oxides such as silica, alumina and mixtures thereof. Other inorganic oxides that may be employed either alone or in combination with the silica or alumina are magnesia, titania, zirconia and the like. Preferably, the catalyst comprises a support material and the support material is alumina or silica, more preferably a silica, most preferably a silica having a surface area between 200 and 900 $m^2/g$ and a pore volume between 0.5 and 4 ml/g.

The invention is also directed to a process for the preparation of the catalyst.

In one embodiment this process comprises the steps of
a. providing a solution of a cocatalyst, an inorganic support material and a metallocene complex
b. reacting the solution of the co-catalyst in a solvent with the metallocene complex to form a pre-catalyst solution, c. adding the pre-catalyst solution to the inorganic support material to form a pre-catalyst mixture and
d. stirring the pre-catalyst mixture at elevated temperature under vacuum to form the catalyst.

In a second embodiment, the process to prepare the catalyst comprises the steps of
a. providing a cocatalyst, an inorganic support material and a metallocene complex
b. adding a solution of the cocatalyst in a solvent to the inorganic support to give a treated support
c. adding the metallocene complex to the treated support to give a pre catalyst mixture
d. stirring the pre catalyst mixture at elevated temperature under vacuum to form the catalyst.

The preferred Al/Zr molar ratio to be employed in the process for preparing the catalyst complex is between 10 and 1000, more preferably between 50 and 500, most preferably between 75 and 300.

Elevated temperature means a temperature between 20 and 150° C., preferably between 40 and 100° C.

The invention is also directed to a process for the preparation of olefin polymers by polymerizing one or more olefins in the presence of the catalyst according to the invention.

In the process to produce olefin polymers the olefin which is polymerized can be one type of olefin or can be mixtures of different olefins. The polymerization thus includes homopolymerization and copolymerization. Examples of olefins are ethylene and α-olefins such as propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto. The α-olefins may optionally contain heteroatoms, like for example O, N, S and P.

Preferably, at least one of the olefins that is polymerized is ethylene. More preferably, a mixture of ethylene and at least one α-olefin having 3 or more carbon atoms is polymerized.

Different types of polyethylene can be prepared with the process according to the invention. For example HDPE, MDPE, LLDPE, UHMWPE which can have a narrow molecular weight distribution or which may also show bimodal molecular weight distributions.

In particular, in the production of LLDPE obtained by copolymerizing ethylene and at least one α-olefin having 3 or more carbon atoms a high molecular weight of the olefin polymer can be obtained. Preferably, the α-olefin is chosen from 1-butene, 1-hexene or 1-octene, more preferably the α-olefin is 1-hexene.

For example an LLDPE having a melt mass flow rate (also known as melt flow index) as determined using ASTM D1238-10 (190° 012.16 kg) which ranges from 0.1 to 125 g/10 min and a density in the range from 900 kg/m$^3$ to less than 940 kg/m$^3$ as determined using ASTM D1505-10 may be obtained. For example, the density of the linear low density polyethylene ranges from about 915 kg/m$^3$ to less than 940 kg/m$^3$, for example between 915 and 925 kg/m$^3$.

For example, the melt flow index of the linear low density polyethylene ranges from 0.3 to 3 g/10 min, for example from 0.5 to 1.5 g/10 min.

Preferably, the α-olefin comonomer is present in an amount of about 5 to about 20 percent by weight of the ethylene-α-olefin copolymer, more preferably in an amount of from about 7 to about 15 percent by weight of the ethylene-α-olefin copolymer.

The solvent or dispersant used in the process to produce olefin polymers may be any organic solvent usually used for the polymerization. Examples of solvents are benzene, toluene, xylene, butane, pentane, hexane, heptane, cyclohexane and methylene chloride.

The polymerization can also be carried out in a process wherein the monomers are solvents or dispersants.

In the process to produce olefin polymers, the polymerization conditions, like for example temperature, time, pressure, monomer concentration can be chosen within wide limits. The polymerization temperature is in the range from −100 to 300° C., preferably 0 to 200° C., more preferably 10 to 120° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, a semicontinuous process or a continuous process and may also be conducted in two or more steps of different polymerization conditions. The polyolefin produced is separated from the polymerization solvent and dried by methods known to a person skilled in the art.

The polymerization may be performed via a gas phase process, via a solution or via a slurry process. Such processes can be carried out in a single reactor or in multiple reactors, for example a cascade of reactors.

The production processes of polyethylene are summarised in "Handbook of Polyethylene" by Andrew Peacock (2000; Dekker; ISBN 0824795466) at pages 43-66. The catalysts can be divided in three different subclasses including Ziegler Natta catalysts, Phillips catalysts and single site catalysts. The latter class is a family of different classes of compounds, metallocene catalysts being one of them. As elucidated at pages 53-54 of said Handbook a Ziegler-Natta catalysed polymer is obtained via the interaction of an organometallic compound or hydride of a Group I-III metal with a derivative of a Group IV-VIII transition metal. An example of a (modified) Ziegler-Natta catalyst is a catalyst based on titanium tetra chloride and the organometallic compound triethylaluminium. A difference between metallocene catalysts and Ziegler Natta catalysts is the distribution of active sites. Ziegler Natta catalysts are heterogeneous and have many active sites. Consequently polymers produced with these different catalysts will be different regarding for example the molecular weight distribution and the comonomer distribution.

The various processes may be divided into solution polymerisation processes employing homogeneous (soluble) catalysts and processes employing supported (heterogeneous) catalysts. The latter processes include both slurry and gas phase processes. The invention is also directed to an olefin polymer, for example polyethylene, preferably LLDPE, MDPE, and HDPE obtainable or obtained by the process of the invention, for example by copolymerizing ethylene and at least one α-olefin in the presence of a catalyst according to the invention.

As defined herein, in linear polyethylene, the term "linear" means that the polymer is substantially linear, and may contain long chain branches.

"Long chain branching" (LCB) means a chain length longer than the short chain branch that results from the incorporation of the α-olefin(s) into the polymer backbone. Each long chain branch will have a similar comonomer distribution as the polymer backbones and can be as long as the polymer backbone to which it is attached.

As a practical matter, current $^{13}C$ nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example, Zimm, G. H. and Stockmayer, W. H., J. Chem. Phys., 17,1301 (1949) and Rudin, A., Modern Methods of Polymer Characterization, John Wiley & Sons, New York (1991 pp. 103-112), or for example: Doerpinghaus, P. J., Baird, G. B., J. Rheol. 47(3), 717-736 (2003).

It has been found that with the metallocene complex of the invention or with the composition of the invention wherein the metallocene complex of the invention is present on a support, it is possible to produce polyethylene from ethylene and at least one α-olefin, for example an α-olefin having up to 8 carbon atoms, with a high incorporation of the at least one α-olefin.

The amount of incorporation of the at least one α-olefin, for example an α-olefin in the polyethylene is expressed by the amount of branches per 1000 carbon atoms.

The presence of short chain branching of up to 6 carbon atoms in length can be determined in ethylene polymers by using $^{13}C$ nuclear magnetic resonance (NMR) spectroscopy and is quantified using the method described by Randall (Rev. Macromol. Chem. Phys., C.29, V. 2 & 3, p. 285-297).

Therefore, the invention also relates to a polyolefin, preferably polyethylene, more preferably linear low density polyethylene (LLDPE). The low density polyethylene, for example LLDPE, preferably has an amount of branches per 1000 carbon atoms as determined using $^{13}C$ NMR of at least 1, for example of at least 2, for example at least 5 and/or for example at most 30, for example at most 25, for example at most 23.

The number average molecular weight (Mn) of the polyolefin, for example polyethylene, for example LLDPE of the invention may vary between wide ranges and may for example be in the range from 1000 to 800000 Da.

For example, the Mn of the polyolefin of the invention may be at least 1500, for example at least 2000, for example at least 20,000, for example at least 50,000 and/or for example at most 150,000, for example at most 110,000, for example at most 100,000, for example at most 70,000.

The weight average molecular weight (Mw) of the polyolefin, for example polyethylene, for example LLDPE of the invention may also vary between wide ranges and may for example be in the range from 1500 to 900000 Da. For example, the Mw of the polyolefin of the invention may be at least 2500, for example at least 10,000, for example at least 50,000, for example at least 100,000 and/or for example at most 400,000, for example at least 350,000, for example at most 300,000, for example at most 250,000.

For purpose of the invention, the Mw and Mn are determined using SEC (Size Exclusion Chromatography) using 1,2,4-trichlorobenzene as an eluent, and calibrated using linear polyethylene standards.

The molecular weight distribution (that is Mw/Mn) of the polyolefin of the invention may for example vary from from 2 to 5, from 2.1 to 4.5 or from 2.5 to 4.

The crystallinity temperature (Tc) of the polyolefin of the invention may for example be in the range from 90 to 120° C. The melt temperature (Tm) of the polyolefin of the invention may for example be in the range from 100 to 140° C.

For purpose of the invention, the $T_m$ and $T_c$ are determined using Differential Scanning calorimetry according to ASTM D 3418-08 using a scan rate of 10° C./min on a sample of 10 mg and using the second heating cycle The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight % to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Other applications may be blow moulding bottles, pipes, caps, closures and the like.

Therefore, in another aspect, the invention also relates to articles comprising the polyolefins obtainable by the process of the invention.

In yet another aspect, the invention also relates to use of the olefin polymers obtainable by the process according to the invention for the preparation of articles, for example for the preparation of films.

In yet another aspect, the invention relates to a process for the preparation of articles using the polyolefin according to the invention.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

EXAMPLES

Test Methods

Melt Index

The melt index is measured according to ASTM D-1238-10 Condition F (190° C., 21.6 kg).

Density

The density is determined according to ISO1872-2. The samples were prepared and pressed according to ISO1872-2 and annealed by boiling in water for half an hour, then left to cool for 16 hours in the same water after which the samples were measured.

Molecular Weight Distribution.

Sample Preparation

The polymer samples were dissolved in 1,2,4-trichlorobenzene (TCB) in the concentration range of 0.3-1.3 mg/ml during 4 h at 160° C. and stabilized with 1 g/l di-tertbutylparacresol (DBPC). The solutions were filtered over a 0.45 μm filter at high temperature (160° C.) prior to injection.

SEC-DV

The separation of the polymer according to molar mass is performed using an Agilent PL220 Size Exclusion Chromatograph (SEC) equipped with 3 Agilent PL Olexis columns. The SEC system is operated at 160° C. and a flow of 1.0 mL/min. Detectors used are a built-in refractive index detector and a PL BV-400 viscometer Branches/1000 C The amount of branches is determined with the aid of FTIR which was calibrated using representative samples that previously have been measured using 13C-NMR.

FTIR of the resulting polymers were measured by converting the PE powder in to a hot-pressed thin film. The film is measured in transmission IR mode. The height of a band corresponding to CH3 bending vibrations (~1380-1375 cm-1) is measured and corrected for the film-thickness using 4400-4000 cm-1 spectral region. The obtained value is then compared with a calibration line. The calibration line is established upfront using reference ethylene/1-olefin polymers characterized by 13C NMR.

Synthesis of Metallocene Complexes 6 different metallocene complexes have been prepared as shown in the next scheme 1:

scheme 1. Metallocene complexes synthesided and used in polymerization of olefins.

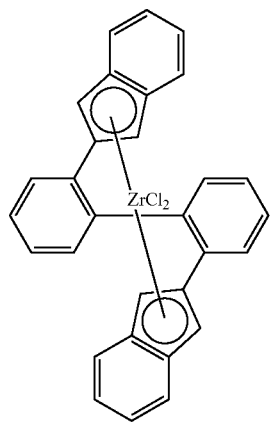

A

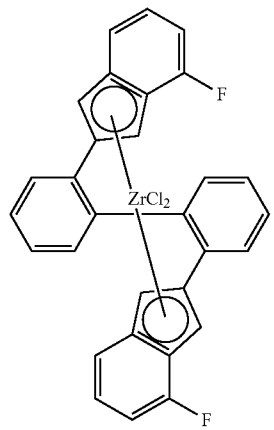

B

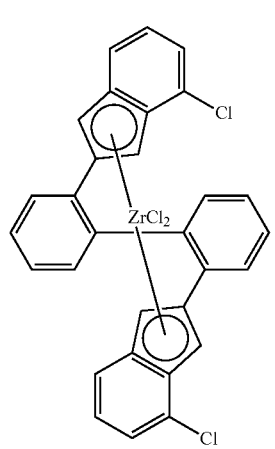

C

-continued

D
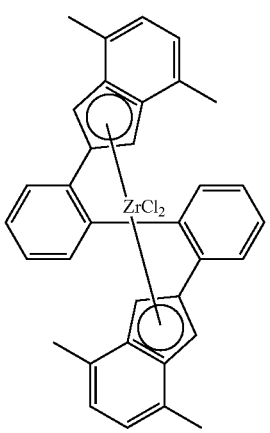

E
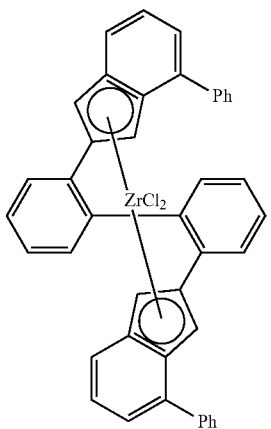

F
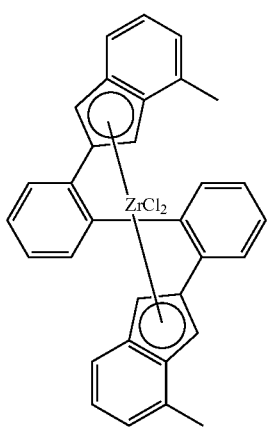

Catalyst A represents a state of the art catalyst, catalysts B, C, D, E and F represent catalysts according to the present invention.

Example 1: Synthesis of Metallocene Complex D [2,2'-Bis($\eta^5$-4,7-dimethyl-1H-inden-2-yl)biphenyl] zirconium dichloride Synthesis of 4,7-Dimethylindan-1-one

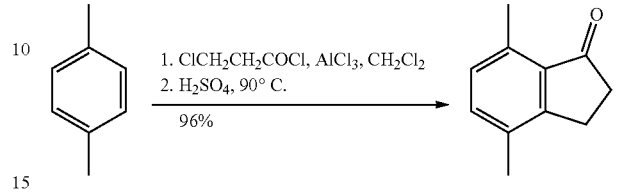

To a stirred suspension of 224 g (1.68 mol) of $AlCl_3$ in 900 ml of dichloromethane a solution of 186 g (1.5 mol) of 3-chloropropanoyl chloride and 148.4 g (1.4 mol) of p-xylene in 175 ml of dichloromethane was added dropwise over 3 h at room temperature. This mixture was stirred additionally for 2 h at room temperature and then poured on 1000 g of crushed ice. The organic layer was separated, and the aqueous layer was extracted with 3×200 ml of dichloromethane. The combined organic extract was washed by aqueous $K_2CO_3$, dried over $K_2CO_3$, passed through a short pad of silica gel 60 (40-63 um), and the elute was evaporated to dryness to give 284 g of dark oily liquid. This liquid was added to 2000 ml of 98% sulfuric acid by vigorous stirring at room temperature. Further on, the resulting dark solution was stirred for 1.5 h at 90° C., cooled to room temperature, and then poured on 4000 g of crushed ice in 4000 ml of cold water. Then, 2 liter of dichloromethane was added. The organic layer was separated, and the aqueous layer was extracted with dichloromethane (100 ml per 900 ml of the aqueous phase). The combined organic extract was washed by cold water, aqueous $K_2CO_3$, dried over $K_2CO_3$, and finally passed through a pad of silica gel 60 (40-63 um). The obtained elute was evaporated to dryness to give a slightly yellowish solid mass. The obtained crude product was re-crystallized from 500 ml of n-hexane (hot→r.t.→0° C., overnight) to give 195 g (87%) of 4,7-dimethylindan-1-one as a white crystalline material. Anal. calc. for $C_{11}H_{12}O$: C, 82.46; H, 7.55. Found: C, 82.77; H, 7.70.

$^1$H NMR ($CDCl_3$): δ 7.22 (d, J=7.5 Hz, 1H), 6.99 (d, J=7.5 Hz, 1H), 2.93 (m, 2H), 2.63 (m, 2H), 2.58 (s, 3H), 2.28 (s, 3H). $^{13}$C{$^1$H} NMR ($CDCl_3$): δ 208.18, 154.63, 135.73, 134.23, 134.02, 132.65, 129.05, 36.49, 24.12, 17.81, 17.23.

Synthesis of 2-Bromo-4,7-dimethyl-1H-indene

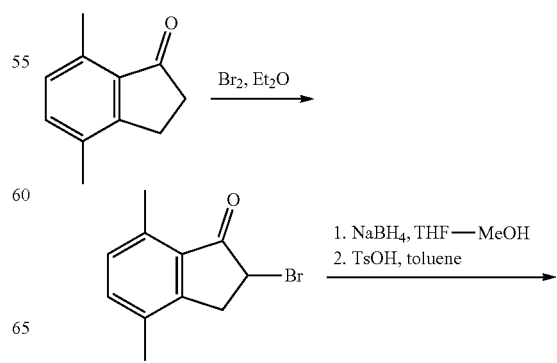

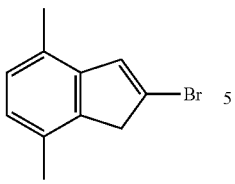

To a solution of 96.1 g (600 mmol) of 4,7-dimethylindan-1-one in 1200 ml of dichloromethane 96 g (601 mmol) of bromine was added dropwise over 1 h. The resulting red solution was stirred overnight at room temperature. The volatiles were removed under vacuum, and the resulting red oily liquid which completely crystallized for a while at room temperature was further used without an additional purification. To a solution of crude 2-bromo-4,7-dimethylindan-1-one in a mixture of 1000 ml of THF and 500 ml of methanol 22.7 g (600 mmol) of NaBH$_4$ was added portionwise for 3 h at 0-5° C. This mixture was stirred overnight at room temperature and then evaporated to dryness. The residue was acidified by 2 M HCl to pH 5-6, and the formed 2-bromo-4,7-dimethylindan-1-ol was extracted with 3×300 ml of dichloromethane. The combined organic extract was dried over Na$_2$SO$_4$ and evaporated to dryness. This product was further used without an additional purification. To a solution of thus obtained brown solid in 1400 ml of toluene 15 g of TsOH was added, and the resulting solution was refluxed using Dean-Stark head for 1.5 h. After cooling to room temperature the reaction mixture was washed by 10% aqueous NaHCO$_3$. The organic layer was separated, and the aqueous layer was additionally extracted with 2×100 ml of dichloromethane. The combined organic extract was evaporated to dryness, and the product was isolated by flash-chromatography on silica gel 60 (40-63 um; eluent: hexanes) followed by re-crystallization from n-hexane. This procedure gave 96.7 g (72%) of 2-bromo-4,7-dimethyl-1H-indene as a white crystalline material.

Anal. calc. for C$_{11}$H$_{11}$Br: C, 59.22; H, 4.97. Found: C, 59.36; H, 5.11.

$^1$H NMR (CDCl$_3$): δ 7.04 (t, J=1.6 Hz, 1H), 6.99 (d, J=7.7 Hz, 1H), 6.91 (d, J=7.7 Hz, 1H), 3.49 (s, 2H), 2.37 (s, 3H), 2.29 (s, 3H). $^{13}$C{$^1$H} NMR (CDCl$_3$): δ 142.46, 141.11, 131.61, 129.68, 128.01, 126.94, 126.13, 123.97, 44.75, 18.23, 18.11.

Synthesis of
2,2'-Bis(4,7-dimethyl-1H-inden-2-yl)biphenyl

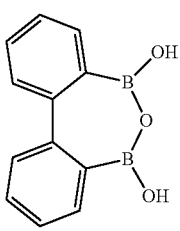

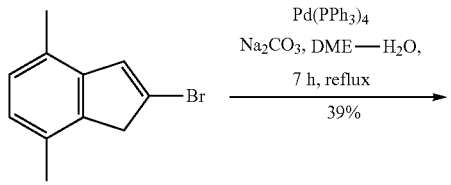

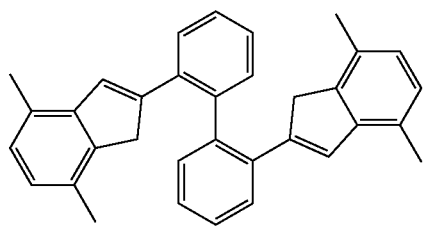

A mixture of 17.8 g (80.0 mmol) of 2-bromo-4,7-dimethyl-1H-indene, 9.67 g (43.2 mmol) of dibenzo[c,e][1,2,7]-oxadiborepine-5,7-diol, 18.2 g (172 mmol) of Na$_2$CO$_3$, 3.23 g (2.8 mmol, 2.8 mol. %) of Pd[PPh$_3$]$_4$, 100 ml of water, and 250 ml of 1,2-dimethoxyethane was refluxed for 7 h. The main part of 1,2-dimethoxyethane was distilled off on rotary evaporator. To the residue 400 ml of dichloromethane and 500 ml of water were added. The organic layer was separated, the aqueous layer was additionally extracted with 100 ml of dichloromethane. The combined organic extract was evaporated to dryness, and the residue was partially purified by flash-chromatography on silica gel 60 (40-63 um, 250 g; eluent: hexanes-dichloromethane=1:1). The product-containing fractions were combined and evaporated to dryness to give yellowish mass. It was dissolved in 70 ml of hot chloroform, and 110 ml of n-hexane was added. White needle-like crystals precipitated from this solution for 6 h at room temperature and then overnight at 5° C. were collected, washed with 50 ml of n-hexane, and dried in vacuum. This procedure gave 5.71 g of 2,2'-bis(4,7-dimethyl-1H-inden-2-yl)biphenyl. The mother liquor was evaporated to dryness, and the residue was dissolved in 10 ml of hot chloroform followed by an addition of 100 ml of n-hexane. Crystals precipitated from this solution overnight at room temperature were collected and dried in vacuum to give 1.15 g of the title compound. Thus, the total yield of 2,2'-bis(4,7-dimethyl-1H-inden-2-yl)biphenyl isolated in this synthesis was 6.86 g (36%).

Anal. calc. for C$_{34}$H$_{30}$: C, 93.11; H, 6.89. Found: C, 93.04; H, 7.02.

$^1$H NMR (CDCl$_3$): δ 7.44-7.40 (m, 2H), 7.39-7.31 (m, 6H), 6.89 (d, J=7.7 Hz, 2H), 6.79 (d, J=7.7 Hz, 2H), 6.21 (s, 2H), 3.16 (d, J=22.4 Hz, 2H), 2.79 (d, J=22.4 Hz, 2H), 2.10 (s, 6H), 2.07 (s, 6H). $^{13}$C{$^1$H} NMR (CDCl$_3$): δ 145.47, 143.58, 141.82, 140.91, 136.45, 130.90, 129.74, 129.05, 128.49, 127.61, 127.47 (two resonances), 127.22, 125.63, 39.91, 18.10, 17.85.

Synthesis of [2,2'-Bis(η$^5$-4,7-dimethyl-1H-inden-2-yl)biphenyl]zirconium dichloride

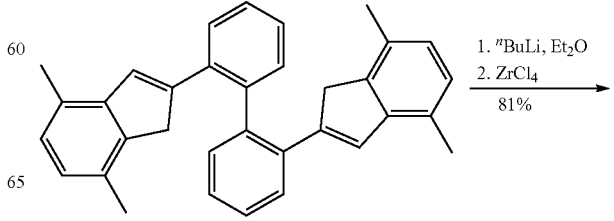

-continued

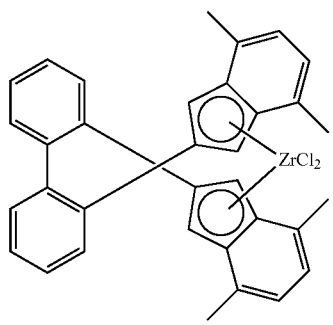

To a suspension of 11.55 g (26.3 mmol) of 2,2'-bis(4,7-dimethyl-1H-inden-2-yl)biphenyl in 450 ml of ether cooled to −60° C. 21.1 ml (52.8 mmol) of 2.5 M"BuLi in hexanes was added in one portion. This mixture was stirred overnight at room temperature. The resulting slightly yellowish solution with a lot of slightly yellowish precipitate was cooled to −50° C., and 6.14 g (26.4 mmol) of $ZrCl_4$ was added. The reaction mixture was stirred for 24 h resulting in yellow solution with yellow heavy precipitate. The resulting mixture was evaporated to dryness, and the residue was heated with 900 ml of toluene. This mixture was filtered while hot through glass frit (G4). On the evidence of NMR spectroscopy the filtrate as well as a huge amount of yellow filter cake contained only single organometallic complex, namely [2,2'-bis(re-4,7-dimethyl-1H-inden-2-yl)biphenyl]zirconium dichloride, which is hardly soluble in common organic solvents (e.g. ca. 0.5 g per 1000 ml of hot toluene). Crystals precipitated from this filtrate for 12 h at room temperature were collected. The solution separated from the crystals was used in the following repetitive extractions of the desired complex from the filter cake. This procedure was repeated until extraction was complete. The combined yellow crystalline material was dried in vacuum. This procedure gave 12.7 g (81%) of [2,2'-bis(re-4,7-dimethyl-1H-inden-2-yl)biphenyl]zirconium dichloride.

Anal. calc. for $C_{34}H_{28}Cl_2Zr$: C, 68.21; H, 4.71. Found: C, 68.40; H, 4.83.

$^1H$ NMR (CDCl$_3$): δ 7.86 (dd, J=7.6 Hz, J=1.4 Hz, 2H), 7.57 (m, 4H), 7.45 (dd, J=7.3 Hz, J=1.6 Hz, 2H), 6.95 (d, J=2.8 Hz, 2H), 6.87 (d, J=7.0 Hz, 2H), 6.80 (d, J=7.0 Hz, 2H), 5.38 (d, J=2.8 Hz, 2H), 2.55 (s, 6H), 1.97 (s, 6H).

Example 2: Preparation of the Silica Supported Metallocene Catalyst and its Characterization (I)

The immobilization of the single site catalyst, A-F (Scheme 1) on silica was performed using Incipient Wetness technique and it involves the following steps:
1. MAO (7.6 mL, 30 w %) is added to 0.244 mmol of single site catalyst and the solution is stirred at room temperature for 30 min
2. The MAO/single site catalyst solution is added drop wise to 5.0 g of silica (ES70X, activated at 600° C. for 4 h) while the mixture is stirred mechanically (incipient wetness)
3. The mixture is stirred at 50° C. for 1 h. Volatiles are evaporated in vacuo at 75° C. for 1 h The elemental compositions of the supported catalysts were measured with XRF.

Comparative Experiment A

In order to compare the catalyst performance of the catalysts according to the present invention and a representative state of the art catalysts, Biph (2-Ind)$_2$ZrCl$_2$ (ref A) was also immobilized on silica using the same protocol mentioned above. Reference patent for state of the art catalyst: U.S. Pat. No. 6,342,622 B1

XRF Results of the Catalysts

| Cat ID | Cat | Al wt % | Si wt % | Zr wt % |
|---|---|---|---|---|
| D | Biph-(2-IndMe$_2$)$_2$ZrCl$_2$ | 13.5 | 30.6 | 0.274 |
| E | Biph-(2-IndPh)$_2$ZrCl$_2$ | 13.1 | 30.1 | 0.292 |
| C | Biph-(2-IndCl)$_2$ZrCl$_2$ | 12.8 | 31.0 | 0.260 |
| B | Biph-(2-IndF)$_2$ZrCl$_2$ | 13.2 | 30.9 | 0.320 |
| Ref A | Biph-(2-Ind)$_2$ZrCl$_2$ | 12.3 | 30.1 | 0.290 |

All the catalysts have similar elemental compositions.

Example 3: Polymerization and Polymer Characterization

Ethylene/1-Hexene Copolymerization in Suspension (PPR)

PPR Polymerization Protocols

Prior to the execution of a library, the 48 PPR cells (reactors) undergo 'bake-and-purge' cycles overnight (8 h at 90-140° C. with intermittent dry N$_2$ flow), to remove any contaminants and left-overs from previous experiments. After cooling to glove-box temperature, the stir tops are taken off, and the cells are fitted with disposable 10 mL glass inserts and PEEK stirring paddles (previously hot-dried under vacuum); the stir tops are then set back in place, the cells are loaded with the proper amounts of toluene (in the range 2.0-3.5 mL), 1-hexene (in the range 0.5-2.0 mL) and MAO solution (100 μL of 0.1 mol L$^{-1}$ in toluene), thermostated at 80° C., and brought to the operating pressure of 65 psig with ethylene. At this point, the catalyst injection sequence is started; proper volumes of a toluene 'chaser', a solution of the precatalyst in toluene (typically in the range 0.01-0.05 mmol L$^{-1}$), and a toulene 'buffer' are uptaken into the slurry needle, and then injected into the cell of destination. The reaction is left to proceed under stirring (800 rpm) at constant temperature and pressure with continuous feed of ethylene for 30 min, and quenched by over-pressurizing the cell with dry air (preferred to other possible catalyst poisons because in case of cell or quench line leaks oxygen is promptly detected by the dedicated glove-box sensor).

After quenching, the cells are cooled down and vented, the stir-tops are removed, and the glass inserts containing the reaction phase are taken out and transferred to a Genevac EZ2-Plus centrifugal evaporator, where all volatiles are distilled out and the polymers are thoroughly dried overnight. Reaction yields are double-checked against on-line monomer conversion measurements by robotically weighing the dry polymers in a Bohdan Balance Automator while still in the reaction vials (subtracting the pre-recorded tare). Polymer aliquots are then sampled out for the characterizations.

GPC Analysis

GPC curves are recorded with a Freeslate Rapid GPC setup, equipped with a set of 2 mixed-bed Agilent PLgel 10 μm columns and a Polymer Char IR4 detector. The upper deck of the setup features a sample dissolution station for up to 48 samples in 10 mL magnetically stirred glass vials, 4 thermostated bays each accommodating 48 polymer solutions in 10 mL glass vials, and a dual arm robot with two heated injection needles. With robotic operation, pre-weighed polymer amounts (typically 1-4 mg) are dissolved in proper volumes of orthodichlorobenzene (ODCB) containing 0.40 mg mL$^{-1}$ of 4-methyl-2,6-di-tert-butylphenol (BHT) as a stabilizer, so as to obtain solutions at a concentration of 0.5 to 1.0 mg mL$^{-1}$. After 2 h at 150° C. under gentle stirring to ensure complete dissolution, the samples are transferred to a thermostated bay at 145° C., and sequentially injected into the system at 145° C. and a flow rate of 1.0 mL min$^{-1}$. In post-trigger delay operation mode, the analysis time is 12.5 min per sample. Calibration is carried out with the universal method, using 10 monodisperse polystyrene samples (Mn between 1.3 and 3700 KDa). Before and after each campaign, samples from a known i-PP batch produced with an ansa-zirconocene catalyst are analyzed for a consistency check.

NMR Characterizations $^{13}$C NMR spectra are recorded with a Bruker Avance 400 III spectrometer equipped with a 5 mm High Temperature Cryoprobe, and a robotic sample changer with pre-heated carousel (24 positions). The samples (20-30 mg) are dissolved at 120° C. in tetrachloroethane-1,2-d$_2$ (0.6 mL), added with 0.40 mg mL$^{-1}$ of BHT as a stabilizer, and loaded in the carousel maintained at the same temperature. The spectra are taken sequentially with automated tuning, matching and shimming. Typical operating conditions for routine measurements are: 45° pulse; acquisition time, 2.7 s; relaxation delay, 5.0 s; 400-800 transients (corresponding to an analysis time of 30-60 min). Broad-band proton decoupling is achieved with a modified WALTZ16 sequence (BI_WALTZ16_32 by Bruker).

Ethylene Homopolymerization Procedure in Slurry

The polymerizations were carried out in a 5 L bench scale batch reactor. The reactor operates under slurry conditions using isobutane as diluent. The 5 liter reactor is filled to 65% of its volume with diluent prior to each experiment. Atmer 163 premixed with 2 equivalents of TiBA was used as anti-fouling agent and TiBA was used as scavenger (0.017 mmol/L). The temperature of the reactor was kept as constant as possible by a thermostat bath. About 100 mg of the immobilised catalysts was then injected into the reactor, and constant ethylene pressure was maintained. After 1 hour of reaction time, the polymers were collected and dried in the vacuum oven (60° C., overnight) before the further analysis.

Ethylene/1-Hexene Copolymerization

Copolymerizations were also carried out in the same experimental set up used for homopolymerization. The same polymerization protocols were used except that specific amount of 1-hexene was fed into the reactor prior to the ethylene feed. After 1 hour of reaction time, the polymers were collected and dried in the vacuum oven (60° C., overnight) before the further analysis.

TABLE 1

Ethylene copolymerization results unsupported catalyst
(Solution polymerisation/homogeneous polymerisation)

| Cat ID | Catalyst | C6 (Vol %) | *Rp | M$_w$ (kg/mol) | PDI | C6 (mol %) |
|---|---|---|---|---|---|---|
| Ref A | Biph(2-Ind)$_2$ZrCl$_2$ | 10 | 478 | 386 | 2.9 | 1 |
| Ref A | Biph(2-Ind)$_2$ZrCl$_2$ | 40 | 160 | 222 | 3.0 | 4.1 |
| B | Biph(2-IndF)$_2$ZrCl$_2$ | 10 | 157 | 264 | 2.5 | 2.1 |
| B | Biph(2-IndF)$_2$ZrCl$_2$ | 40 | 34 | 147 | 2.2 | 8.0 |
| C | Biph(2-IndCl)$_2$ZrCl$_2$ | 10 | 222 | 115 | 2.5 | 4.4 |
| C | Biph(2-IndCl)$_2$ZrCl$_2$ | 40 | 58 | 124 | 2.2 | 8.9 |
| D | Biph(2-IndMe$_2$)$_2$ZrCl$_2$ | 10 | 601 | 401 | 2.8 | 2.0 |
| D | Biph(2-IndMe$_2$)$_2$ZrCl$_2$ | 40 | 136 | 92 | 2.2 | 12.7 |

*Rp = Productivity in kg mmol$_{cat}^{-1}$ [C$_2$H$_4$]$^{-1}$ h$^-$, Polymerisation time = 30 min, temperature = 80° C., MAO = 2 mM.
A = State of the art catalyst Hexene Incorporation is Higher in the Case of B, C, and D Compared to State of the Art Catalyst A Ethylene homo and copolymerization results are given in Table 2.

TABLE 2

Homo and copolymerization results of supported catalysts*

| Cat ID | 1-hexene (mL) | Activity (gPE/gcat) | MFI 21.6 | Density Kg/m$^3$ | Branches/ 1000C | Mw (kg/mol) | Mn (kg/mol) | Mw/Mn |
|---|---|---|---|---|---|---|---|---|
| D | 0 | 1311 | 2.2 | 950 |  | 240 | 65 | 3.8 |
| D | 75 | 2178 | 2.8 | 934 | 1.8 | 220 | 67 | 3.3 |
| E | 0 | 1167 | 0.92 | 952 |  | 210 | 59 | 3.5 |
| E | 75 | 1843 | 1.6 | 935 | 2.3 | 245 | 70 | 3.5 |
| C | 75 | 1104 | 2.4 | 933 | 2.3 | 190 | 58 | 3.3 |
| B | 75 | 1458 | 3.7 | 933 | 2.5 | 165 | 48 | 3.4 |
| Ref A | 0 | 2766 | 6.6 | 950 |  | 280 | 63 | 4.4 |
| Ref A | 75 | 1049 | 4.6 | 936 | 1.6 | 175 | 54 | 3.2 |

*Polymerization Temperature = 80° C., Polymerization time = 1 hour, isobutane as diluent.
Catalyst Ref A represents the comparative example- reference state of the art catalyst.

The invention claimed is:

1. A metallocene complex according to formula I

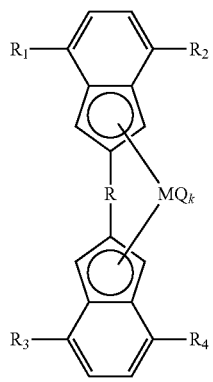

Formula I wherein
M is a metal selected from lanthanides or transition metals from group 3, 4, 5 or 6 of the Periodic System of the Elements,
Q is an anionic ligand to M,
k is the number of Q groups and equals the valence of M minus 2,
R is a bridging group containing at least one carbon atom, selected from a 2,2' biphenylgroup or a substituted 2,2' biphenylgroup, bonded to the indenyl moiety at the 2-position and,
$R_1$, $R_2$, $R_3$ and $R_4$ are each independently selected from the group consisting of hydrogen, a halogen atom and a C1-C20 hydrocarbyl group, and wherein at least one of $R_1$ and $R_2$ is not hydrogen, and at least one of $R_3$ and $R_4$ is not hydrogen.

2. The metallocene complex according to claim 1, wherein M is Ti, Zr or Hf.

3. The metallocene complex according to claim 1, wherein Q is chlorine or a methyl group.

4. The metallocene complex according to claim 1, wherein $R_1$, $R_2$, $R_3$ and $R_4$ are each independently selected from hydrogen, fluorine, chlorine, methyl, ethyl, propyl, or phenyl.

5. A catalyst for polymerizing olefins into polyolefins, wherein the catalyst is formed by reacting a metallocene complex according to claim 1 and a cocatalyst, wherein the cocatalyst is an aluminum or boron containing cocatalyst.

6. The catalyst according to claim 5, wherein the catalyst comprises an inorganic support.

7. A process for polymerizing olefins, which comprises the steps of providing a polymerization reactor,
contacting at least one monomer, a metallocene complex as defined in claim 1 and a cocatalyst to prepare a polyolefin under polymerization conditions.

8. The process according to claim 7, wherein at least ethylene and an alfa-olefin are present as monomers to prepare a polyethylene.

9. The catalyst of claim 5, wherein the cocatalyst is an aluminoxane, an aluminum alkyl compound, a trialkylborane, a perfluorophenylborane or a perfluorophenylborate.

10. The catalyst according to claim 9, wherein the catalyst comprises an inorganic support.

11. A process for polymerizing olefins, which comprises the steps of providing a polymerization reactor,
contacting at least ethylene and an alfa-olefin as comonomers, a metallocene complex as defined in claim 10 and a cocatalyst to prepare a polyolefin under polymerization conditions.

12. The metallocene complex according to claim 2, wherein Q is chlorine or a methyl group.

13. The metallocene complex according to claim 12, wherein $R_1$, $R_2$, $R_3$ and $R_4$ are each independently selected from hydrogen, fluorine, chlorine, methyl, ethyl, propyl, or phenyl.

14. A catalyst for polymerizing olefins into polyolefins, wherein the catalyst is formed by reacting a metallocene complex according to claim 13 and a cocatalyst, wherein the cocatalyst is an aluminum or boron containing cocatalyst.

15. The catalyst of claim 14, wherein the cocatalyst is an aluminoxane, an aluminum alkyl compound, a trialkylborane, a perfluorophenylborane or a perfluorophenylborate.

16. The catalyst according to claim 14, wherein the catalyst comprises an inorganic support.

17. A process for polymerizing olefins, which comprises the steps of providing a polymerization reactor,
contacting at least one monomer, a metallocene complex as defined in claim 14 and a cocatalyst to prepare a polyolefin under polymerization conditions.

18. The process according to claim 7, wherein at least ethylene and an alfa-olefin are present as monomers to prepare a polyethylene.

* * * * *